(12) United States Patent
Fraundorfer

(10) Patent No.: US 8,431,076 B2
(45) Date of Patent: Apr. 30, 2013

(54) STERILISATION APPARATUS

(75) Inventor: Mark Robert Fraundorfer, Mt. Maunganui (NZ)

(73) Assignee: Tristel PLC, Snailwell, Cambridgeshire (GB)

( * ) Notice: Subject to any disclaimer, the term of this patent is extended or adjusted under 35 U.S.C. 154(b) by 694 days.

(21) Appl. No.: 12/376,815

(22) PCT Filed: Aug. 15, 2007

(86) PCT No.: PCT/NZ2007/000220
§ 371 (c)(1),
(2), (4) Date: Apr. 6, 2010

(87) PCT Pub. No.: WO2008/020770
PCT Pub. Date: Feb. 21, 2008

(65) Prior Publication Data
US 2010/0189598 A1     Jul. 29, 2010

(30) Foreign Application Priority Data

Aug. 15, 2006  (NZ) ........................ 549214

(51) Int. Cl.
*A61L 2/00* (2006.01)
(52) U.S. Cl.
USPC ............ 422/28; 422/1; 422/50; 422/500; 422/501; 134/25.1
(58) Field of Classification Search ........... 422/1, 28, 422/50, 500–501; 134/43, 58–59, 25.1
See application file for complete search history.

(56) References Cited

U.S. PATENT DOCUMENTS

| | | | |
|---|---|---|---|
| 4,601,300 A | 7/1986 | Sundheimer | |
| 4,763,678 A | 8/1988 | Ott | |
| 5,174,970 A | 12/1992 | Santasalo | |
| 5,732,821 A | 3/1998 | Stone et al. | |
| 5,882,589 A | 3/1999 | Mariotti | |
| 6,896,149 B1 | 5/2005 | Berry III | |
| 2001/0042561 A1 | 11/2001 | Kaketani et al. | |
| 2004/0253140 A1 | 12/2004 | Wagemann et al. | |

FOREIGN PATENT DOCUMENTS

| | | |
|---|---|---|
| EP | 1 629 765 A1 | 3/2006 |
| FR | 2 803 755 | 7/2001 |
| JP | 10-136957 | 5/1998 |
| WO | WO 97/32610 | 9/1997 |

OTHER PUBLICATIONS

Supplementary European Search Report for corresponding European Application No. EP 07 83 4828. Sep. 28, 2010.

*Primary Examiner* — Jyoti Nagpaul
(74) *Attorney, Agent, or Firm* — Merchant & Gould P.C.

(57) ABSTRACT

The present invention relates to a sterilization and disinfection apparatus. In particular, the present invention relates to a sterilization and disinfection apparatus for surgical equipment.

Thus preferred embodiments may have a number of advantages over the prior art which can include:
  reduced risk of spillage of the sterilization fluid outside the sterilization apparatus;
  reduced risk of contamination of the equipment after sterilization through inadvertent contact with the equipment by the user;
  economy of use of the sterilization fluid;
  improved convenience of transport and storage of sterilized equipment in the sterilization apparatus;
  automatic override procedure to reduce the risk of overexposure of the equipment to the sterilization fluid if the correct sterilization cycle is not followed;
  automatic control of contact time of the equipment with the sterilization fluid to avoid over processing and resultant damage; and
  data logging to provide traceability of the previous sterilization cycles used.

15 Claims, 7 Drawing Sheets

STERILISATION APPARATUS

STATEMENT OF CORRESPONDING APPLICATIONS

This application is a National Stage Application of PCT/NZ2007/000220, filed Aug. 15, 2007, which claims benefit of Serial No. 549214, filed Aug. 15, 2006 in New Zealand and which application(s) are incorporated herein by reference. To the extent appropriate, a claim of priority is made to each of the above disclosed applications.

TECHNICAL FIELD

The present invention relates to a sterilisation and disinfection apparatus. In particular, the present invention relates to a sterilisation and disinfection apparatus for surgical equipment.

BACKGROUND ART

Surgical equipment such as endoscopes requires washing and sterilisation each time before use. Existing methods of washing and sterilisation include placing the endoscope in relatively large flat bottomed trays and submerging in sterilisation fluid such as glutaraldehyde, chlorine dioxide, peracetic acid, hydrogen peroxide, ozone or ozonated and super oxidised water. The time period the equipment is in contact with the sterilisation fluid is timed and the liquid drained from the tray by tipping the tray to drain the fluid into a storage tank or down the sink.

A disadvantage with such a method is spillage or splashing of the sterilisation fluids when draining the trays after sterilisation. As the sterilisation fluids are generally corrosive and can be dangerous to health and damaging to the surrounding sterilisation area.

A second disadvantage is the risk of contamination of the equipment after sterilisation via inadvertent touching by the user. Further disadvantages include the inconvenience of manually lifting and tipping trays filled with sterilisation fluid and relatively heavy equipment and the cost associated with using large volumes of sterilisation fluid.

Endoscope sterilisation apparatus are known. Conventional apparatus require the user to know the correct procedure in terms of exposure time of the particular piece of equipment being sterilised to the particular sterilisation fluid needed. In addition such apparatus do not provide for automatic data logging of the previous sterilisation procedures to provide traceability for quality control.

All references, including any patents or patent applications, cited in this specification are hereby incorporated by reference. No admission is made that any reference constitutes prior art. The discussion of the reference states what their authors assert, and the applicants reserve the right to challenge the accuracy and pertiency of the cited documents. It will be clearly understood that, although a number of prior art publications are referred to herein, this reference does not consitute an admission that any of these documents forms parts of the common general knowledge in the art, in New Zealand or in any other country.

It is acknowledged that the term 'comprise' may, under varying jurisdictions, be attributed with either an exclusive or an inclusive meaning. For the purpose of this specification, and unless otherwise noted, the term 'comprise' shall have an inclusive meaning—i.e. that it will be taken to mean an inclusion of not only the listed components it directly references, but also other non-specified components or elements. This rationale will also be used when the term 'comprised' or 'comprising' is used in relation to one or more steps in a method or process.

It is an object of the present invention to address the foregoing problems or at least to provide the public with a useful choice.

Further aspects and advantages of the present invention will become apparent from the ensuing description which is given by way of example only.

DISCLOSURE OF INVENTION

According to one aspect of the present invention there is provided a sterilisation apparatus which includes:
 a sterilisation compartment formed from at least one wall and base; and
 a spill compartment formed from at least one wall and base;
the sterilisation apparatus characterised in that the wall(s) of the sterilisation compartment is/are contained within the wall(s) of the spill compartment.

In preferred embodiments the sterilisation apparatus may further include a drain outlet and associated valve adapted so as to drain the sterilisation fluid from the sterilisation compartment and/or the spill compartment.

In preferred embodiments the sterilisation apparatus may further include a drain control device which is configured to operate the opening and closing of the drain outlet to control exposure time of equipment to the sterilisation fluid.

For the purposes of the specification the term "sterilisation" or grammatical variations thereof may refer to the making of an object free from live microorganisms such as bacteria and up to a 6 logarithmic reduction in endospores of spore-forming bacteria with the use of a sterilisation fluid.

For the purposes of the specification the term "equipment" or grammatical variations thereof may refer to pieces of equipment, such as endoscopes, and associated cables that require sterilisation before and/or after use.

In preferred embodiments the spill compartment may be separated from the sterilisation compartment by a wall lower in height than that of the external base tray wall.

In preferred embodiments the base tray may have profiling on the inside surface of the base tray via a contact means to contact and retain the equipment to hold the equipment substantially above the base tray to maximise the exposure of the equipment with the sterilisation fluid.

In preferred embodiments the contact means may be a raised profile to provide a contact surface for the equipment in the base tray.

In more preferred embodiments the raised profile may be ribs and guide tabs.

In preferred embodiments the inside surface of the base tray may be pre-moulded to substantially conform to the general shape of the equipment to be sterilised.

In this way a minimal volume of sterilisation fluid is used for each sterilisation cycle.

In preferred embodiments the drain control device may operate the opening and closing of the drain outlet via a clamp, clasp, catch, fastener or valve.

In preferred embodiments the drain control device may operate the opening and closing of the drain outlet via a valve.

It is envisaged the drain control device may come in a variety of different forms without departing from the scope of the present invention.

In some embodiments the drain control device may include a control device along with an optional display device. For example, the control device may include a keypad and the display device may be in the form of light emitting diodes, liquid crystal display, or similar.

In preferred embodiments, the drain control device may include a timer to time the stages of the sterilisation cycle and interact with the control and display devices.

In preferred embodiments, the drain control device may follow an automatic override procedure wherein the sterilisation fluid is drained from the sterilisation compartment if the correct sequence of events of the sterilisation cycle is not followed.

In this way the equipment is prevented from being in contact with the potentially corrosive sterilisation fluid for extended periods.

In preferred embodiments, the drain control device may include a CPU or other processing device or logic unit.

In more preferred embodiments, the drain control device may include a remote CPU or other processing device or logic unit.

In preferred embodiments, the drain control device may log the parameters of the previous sterilisation cycles.

In more preferred embodiments, the drain control device may be connected to a printer or Universal Serial Bus (USB). In this way the stored logged parameters may be transferred to a remote device or printed out.

In this way traceability of the previous sterilisation cycles followed can be achieved.

In preferred embodiments, the drain control device may include a liquid level sensor so that the display device may indicate to a user when a preferred amount of sterilisation fluid has been added to the sterilisation apparatus.

In preferred embodiments the base tray may have a lid which engages with the base tray via a lid engagement means.

In more preferred embodiments the lid engagement means may be a lip on the circumference of the lid which engages with the outer wall of the base tray.

In preferred embodiments the lid may have a handle on the top surface of the lid.

In preferred embodiments the lower surface of the tray may be profiled so a portion of the lower surface may contact the sterilisation fluid when the base tray is filled and the lid engaged. In this way a portion of lid may be sterilised and prevent inadvertent contamination of the sterilised equipment on touching the sterilised lid portion.

In preferred embodiments the lid may not contact the internal wall of the base tray when the lid is engaged with the base tray.

In preferred embodiments the base tray may have a tray engaging means to enable one base tray to engage with another base tray.

In more preferred embodiments the tray engaging means may be a raised rib around the circumference of the bottom of the base tray which engages with a corresponding recess on the lid and/or the internal wall of another base tray.

In this way the base trays with or without lids may be stacked on top of each other to save space when storing multiple base trays.

In preferred embodiments the lid may have a lid engaging means to enable one lid to engage with another lid.

In more preferred embodiments the lid engaging means may be a raised rib around the circumference of the bottom of the lid which engages with a corresponding recess on the top of another lid.

In this way lids which are not attached to base trays may be stacked on top of each other to save space when storing multiple lids.

In preferred embodiments the outer wall of the base tray may have an exit for a cable of equipment to be sterilised. In more preferred embodiments the outer wall of the base tray may have a cut-out exit for a cable of equipment to be sterilised. It is envisaged the cut-out exit may be filled by reversible attachment of a corresponding tab into the cut-out when the cut-out exit is not needed.

In preferred embodiments the base tray and lid may be made of plastic.

The plastic used in the construction of the base tray and lid has to withstand the sterilisation fluids used without degradation and be able to be sterilised by autoclaving at temperatures up to 135° C.

In preferred embodiments the base tray may have an associated container which realisably attaches to the sterilisation compartment so that its upper edges are lower than or flush with the upper edge of the sterilisation compartment. In more preferred embodiments the associated container may have perforations. In this way addition of sterilisation fluid to the sterilisation compartment will also fill the associated container and draining of the sterilisation compartment will also drain the associated container.

It is envisaged the associated container will enable small parts associated with the equipment to be conveniently sterilised and retrieved from the base tray.

In use the sterilisation fluid may be selected from the group including: glutaraldehyde, chlorine dioxide solution, peracetic acid, hydrogen peroxide solution, ozone or ozonated and super oxidised water.

In preferred embodiments the sterilisation fluid may be chlorine dioxide solution.

In more preferred embodiments the sterilisation fluid may be chlorine dioxide solution prepared before use by addition of pre-aliquoted amounts of sodium chlorite and acid solution.

In preferred embodiments the sterilisation apparatus is sold as a kit assembly together with a jug for preparation of the chlorine dioxide solution before use.

In this way an exact amount of chlorine dioxide solution is prepared to fill the sterilisation compartment when a piece of equipment is located in the sterilisation apparatus for sterilisation.

According to another aspect of the present invention there is provided a method for timed sterilisation of equipment using the sterilisation apparatus of the present invention including the steps:

1. Optional step of removing the lid of the sterilisation apparatus;
2. Place equipment in the sterilisation apparatus;
3. Add sterilisation fluid to the equipment in the sterilisation compartment;
4. Operating the drain control device to select the desired sterilisation time;
5. Remove the equipment from the sterilisation apparatus for use.

Thus preferred embodiments may have a number of advantages which can include:
   reduced risk of spillage of the sterilisation fluid outside the sterilisation apparatus;
   reduced risk of contamination of the equipment after sterilisation through inadvertent contact with the equipment by the user;
   economy of use of the sterilisation fluid;
   improved convenience of transport and storage of sterilised equipment in the sterilisation apparatus;
   automatic override procedure to reduce the risk of overexposure of the equipment to the sterilisation fluid if the correct sterilisation cycle is not followed;

automatic control of contact time of the equipment with the sterilisation fluid to avoid over processing and resultant damage; and data logging to provide traceability of the previous sterilisation cycles used.

The present invention addresses the problems identified in the prior art above of spillage of the sterilisation fluids when draining the base tray after sterilisation, risk of contamination of the equipment after sterilisation via inadvertent touching by the user, inconvenience of manually lifting and tipping trays filled with sterilisation fluid and relatively heavy equipment, inconvenience of transport and storage of equipment after sterilisation, increased cost associated with using large volumes of sterilisation fluid, non-automatic control of the time the equipment is in contact with the sterilisation fluid and lack of traceability of previous sterilisation procedures used.

BRIEF DESCRIPTION OF DRAWINGS

Further aspects of the present invention will become apparent from the ensuing description which is given by way of example only and with reference to the accompanying drawings in which.

BEST MODES FOR CARRYING OUT THE INVENTION

Figure 1:
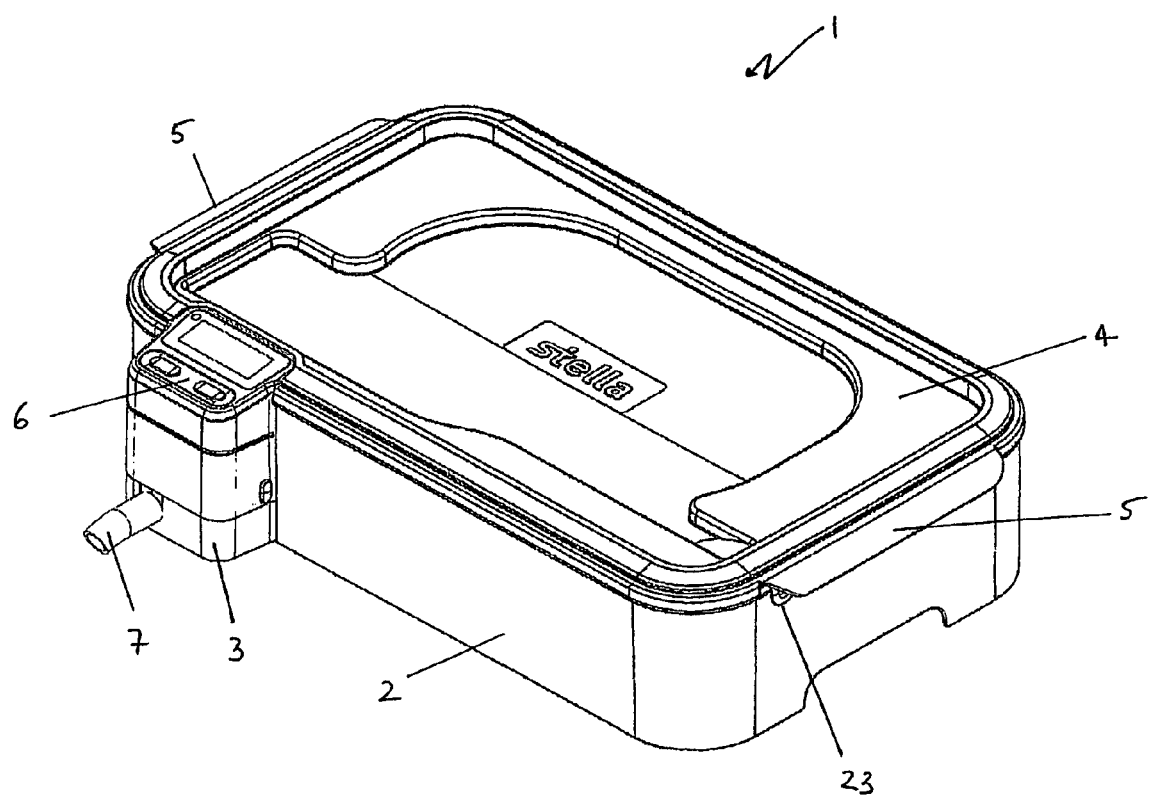
FIG. 1: shows a perspective view of a sterilisation apparatus of the present invention with the lid of the base tray and drain control device engaged.
Figure 2:
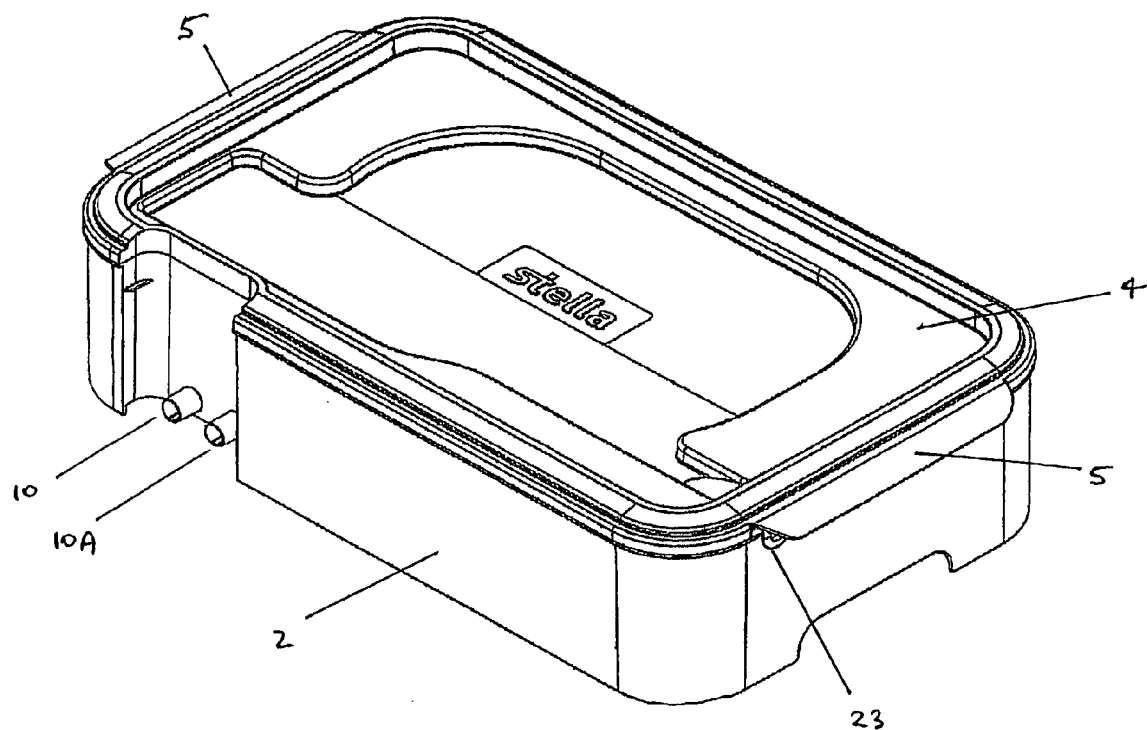
FIG. 2: shows a perspective view of the sterilisation apparatus shown in FIG. 1 without the drain control device engaged.

The invention is now described in relation to one preferred embodiment of the present invention as shown in FIGS. 1 to 6. It should be appreciated that the invention may be varied from the Figures without departing from the scope of the invention.

Referring to FIGS. 1 to 6, the sterilisation apparatus is generally indicated by arrow 1 and includes a base tray 2 with an integral drain control device 3. A lid 4 has two moulded handles 5 to aid in the lid 4 removal. A control device in the form of a keypad 6 and internal timer (not shown) controls the operation of the opening and closing of the drain outlet in the form of a flexible tube 7 (a standard medical suction tube) via a ball valve 8. A display device in the form of a display panel 9 displays text message prompts throughout the sterilisation cycle. The flexible tube 7 is attached to two drain ports 10 and 10A which in turn is connected to an inner sterilisation compartment 11 and an outer spill compartment 12. Both compartments are separated by an internal wall 13 lower in height than the base tray outer wall 14. In this way any spilled sterilisation fluid is collected in the spill compartment 12 and not over the side of the base tray 2.

Figure 3:
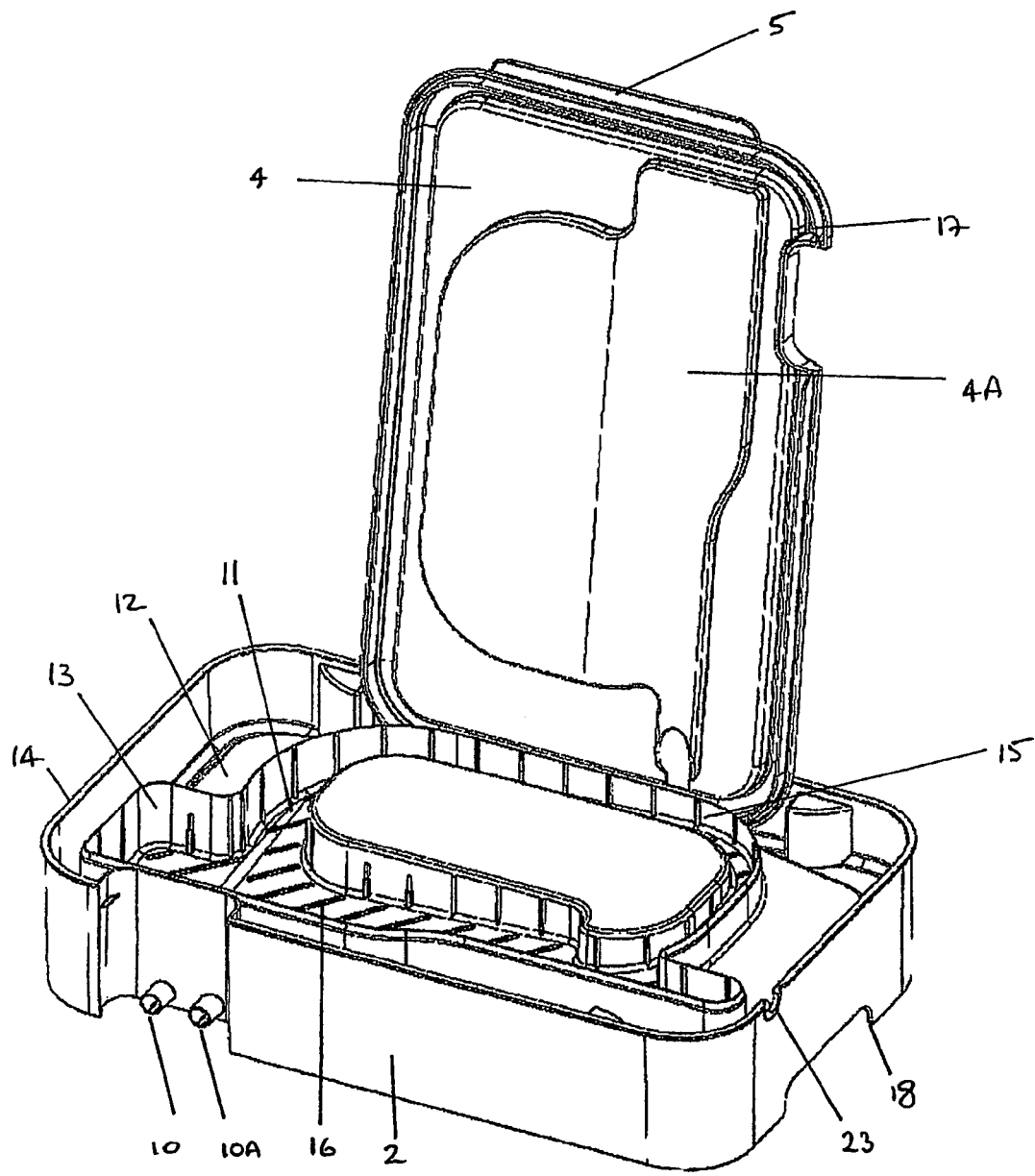
FIG. 3: shows a perspective view of the sterilisation apparatus shown in FIG. 2 with the lid of the base tray in an open position.
Figure 4:
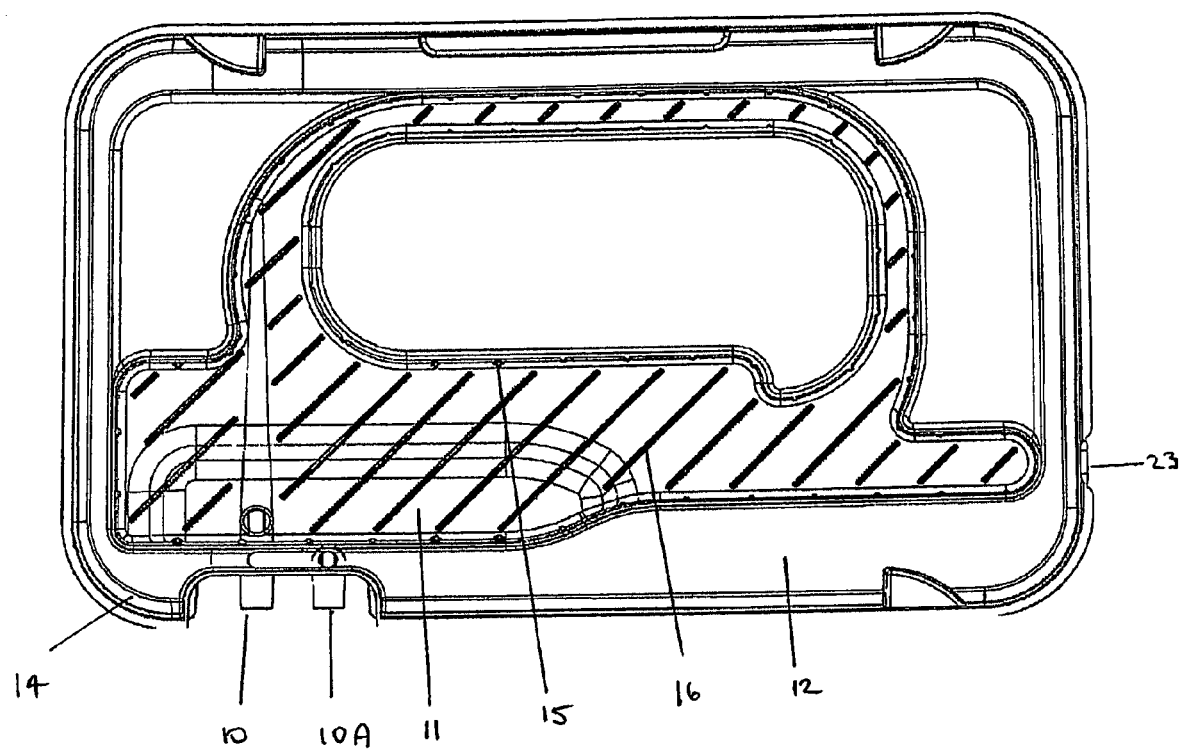
FIG. 4: shows a plan view of a sterilisation apparatus of the embodiment shown in FIG. 2 with the lid of the sterilisation tray removed.

Referring to FIGS. 3 and 4 the sterilisation compartment 11 has guides 15 and raised profiles in the form of ribs and guides 16 which act as a contact and positioning surface for the equipment in the form of a flexible endoscope (not shown) and associated cables (not shown) such that the equipment is maintained in a position having minimal contact with the base tray 2 during the sterilisation procedure. The cable of the equipment may be placed external to the sterilisation apparatus 2 if required.

Figure 5:
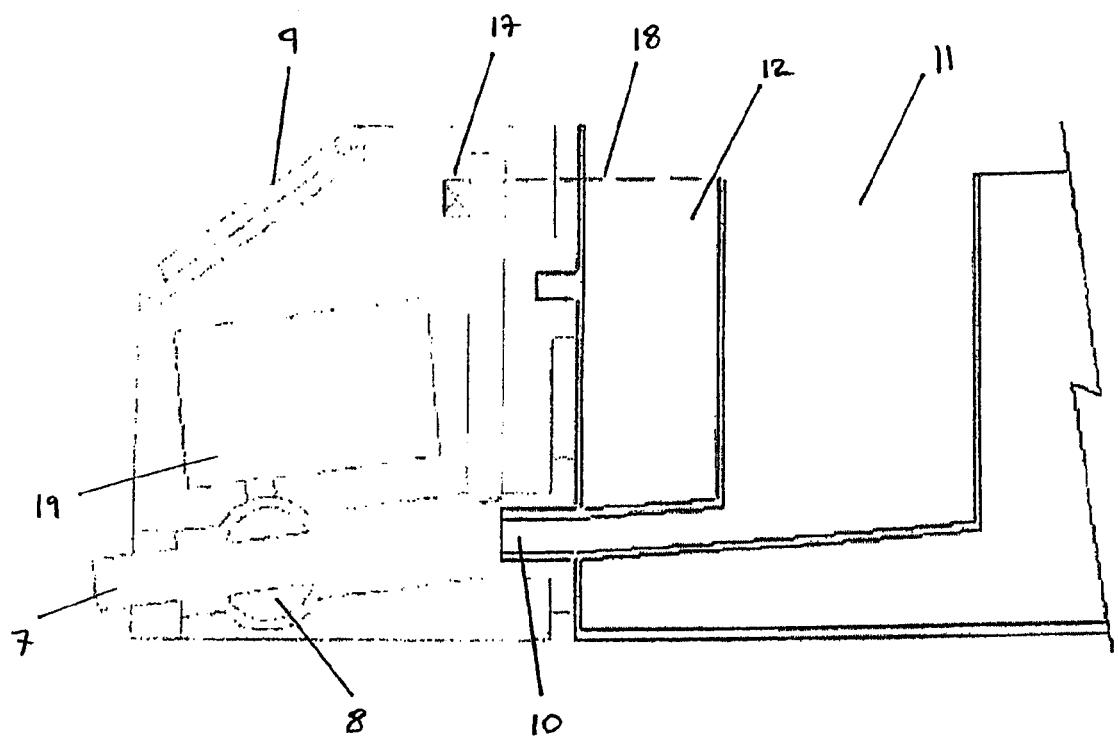
FIG. 5: shows a section side view of the sterilisation apparatus of the embodiment shown in FIG. 1.
Figure 6:
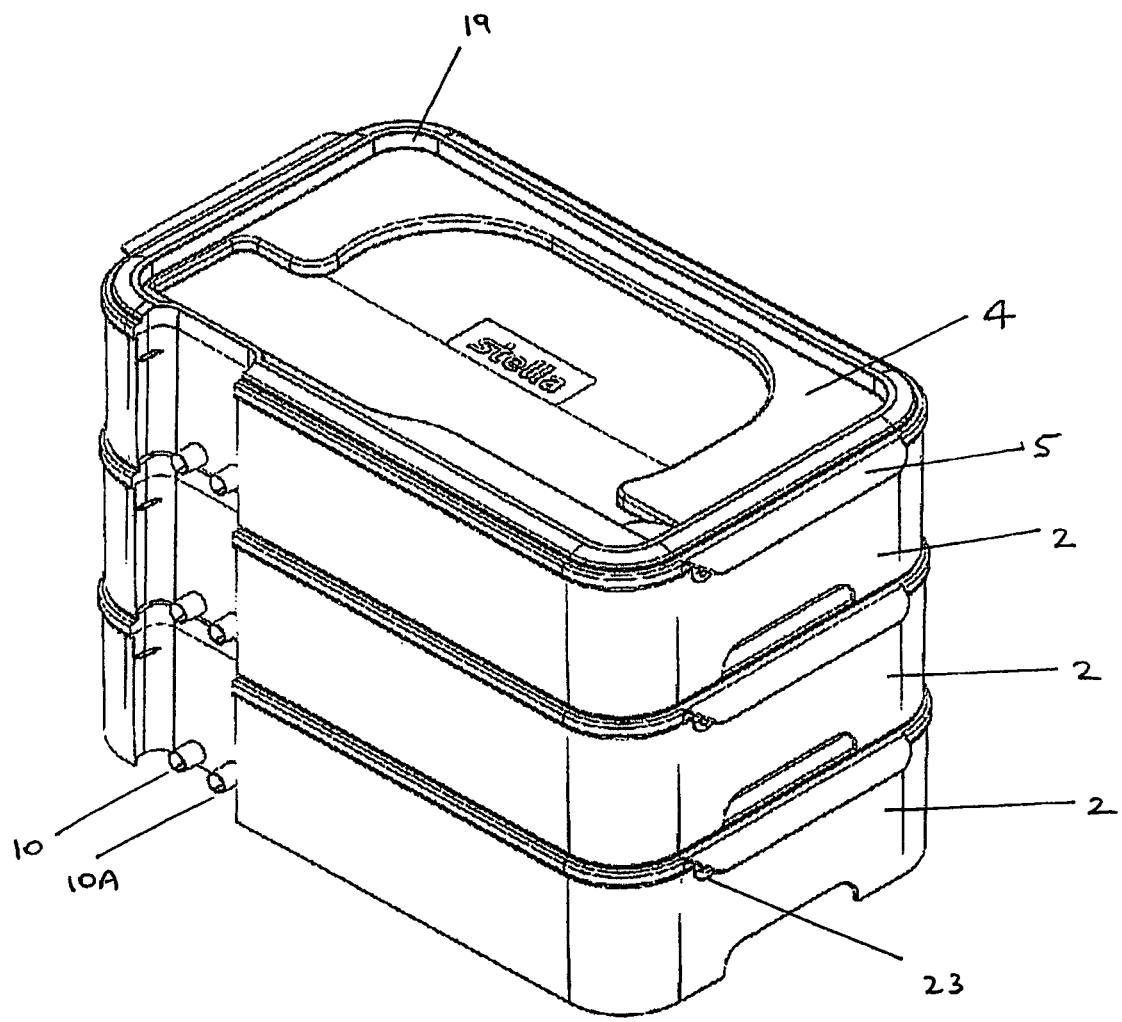
FIG. 6: shows a perspective view of multiple stacked sterilisation apparatus of the embodiment shown in FIG. 2.

Referring to FIG. 5, the drain control device 3 incorporates a liquid level sensor 17 which senses when the level of sterilisation fluid reaches a fill level line 18. Feedback to a CPU (not shown) in the drain control device 3 causes a text prompt on the display panel 9 to alert the user that the required amount of sterilisation fluid has been added to the inner sterilisation compartment 11.

A motor 19 in the drain control device 3 (with associated micro switch and gear box) enables opening and closing of the drain outlet 7 via disengaging or engaging of the ball valve 8 respectively.

The lid 4 engages with the base tray 2 via a lid engagement lip 20 which engages with the outer wall of the base tray 2.

A portion 4A of the lower surface of the lid 4 is profiled to contact the sterilisation fluid when the base tray 2 is filled and the lid 4 is engaged during the sterilisation cycle. In this way the portion 4A of lid is sterilised and prevents inadvertent contamination of the sterilised equipment on touching the sterilised lid portion 4A.

Figure 7:
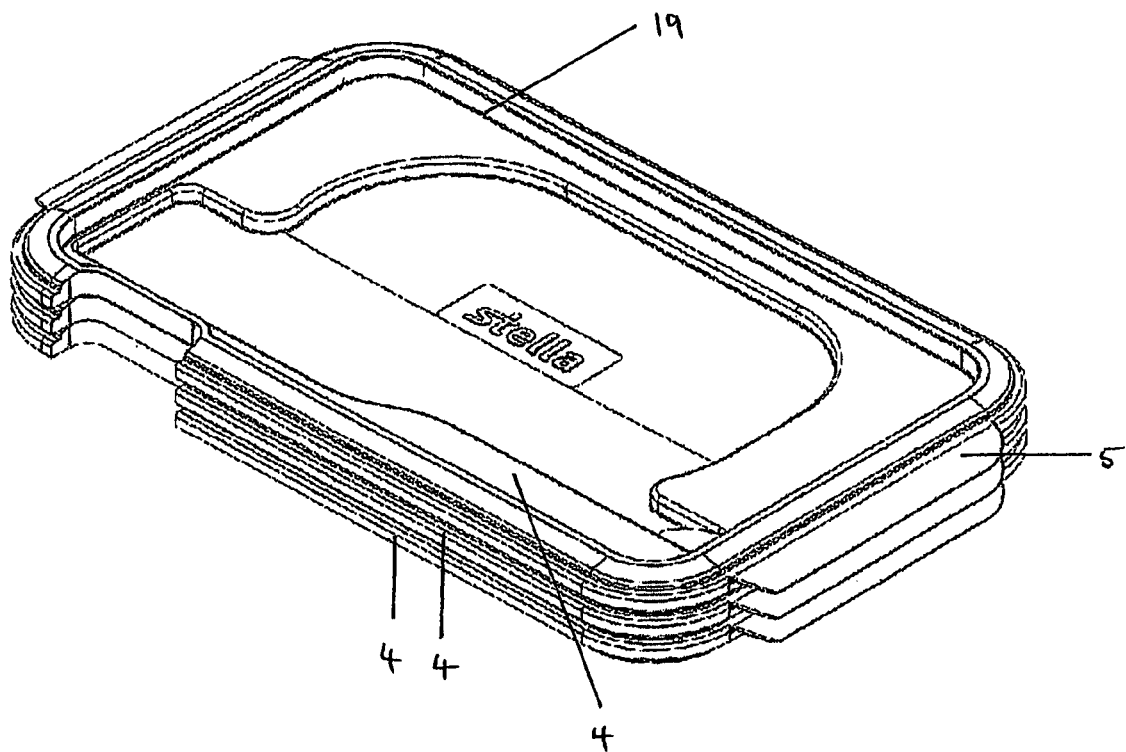
FIG. 7 shows a perspective view of multiple stacked lids of the sterilisation apparatus of the embodiment shown in FIG. 1.

A tray engaging rib 21 is positioned around the circumference of the bottom of the base tray 2 to engage with a groove 22 associated with the lid 4 of the base tray 2, such that sterilisation apparatus (see FIG. 6) or the lids 4 (see FIG. 7) can be stacked one on top of another to save space when not in use.

A cut-out cable exit 23 in the outer wall 14 of the base tray 2 allows exit of the cable of the equipment being sterilised and still enables the lid 4 of the sterilisation apparatus 1 to be engaged with base tray 2 during the sterilisation cycle.

EXAMPLE 1

The following is the procedure followed for timed sterilisation of equipment using the sterilisation apparatus of the present invention:

1.0 Sterilisation Apparatus Preparation
1.1 Removing the lid of the sterilisation apparatus;
1.2 Attaching one end of the drain outlet channel to the sterilisation apparatus;
1.3 Attaching the other end of the drain outlet channel is located into a container or sink in preparation of drainage of the sterilisation fluid;
2.0 Sterilisation Cycle
2.1 The 'ON' button is pushed;
2.2 The drain control device closes the drain outlet via the interaction means;
2.3 A 5 minute timer starts till the release of the interaction means;
2.4 A text message is shown on the display panel to prompt the continuation of the process;
2.5 The equipment is placed into the base tray, making sure it is seated correctly;
2.6 Sterilisation fluid is prepared in an associated mixing jug;
2.7 Sterilisation fluid is poured into the sterilisation compartment until it over flows into the spill compartment (providing a visual indication of adequate filling of the sterilisation compartment). In addition a liquid sensor alerts the user via an alarm when an adequate volume of sterilisation fluid has been added to the base tray;
2.8 A 5 minute timer starts cancelling the timer in 2.3. A text message "STERILISING" is shown on the display panel.
2.9 The lid is placed on the sterilisation apparatus;
2.10 After 5 minutes the interaction means releases accompanied by an audible signal;
2.11 A text message "COMPLETE" is shown on the display panel;
2.12 The 'OFF' button is pushed;
2.13 The interaction means stays released;
2.14 The drain control device records date, time and cycle number;
2.15 The drain control device turns off;
3.0 Default Drain Procedure
3.1 If the 'START' button is not pushed within a 5 minute period from the 'ON' button being pushed;
3.2 The clamp is released by the drain control device;
3.3 A text message "FAIL" is shown on the display panel;
3.4 An alarm sounds for 5 minutes or until the "OFF" button is pushed;
3.5 The drain control device records date, time and fail;
3.6 The drain control device turns off;
3.7 The user can start the sterilisation cycle again by pressing the "OFF" button and then the "ON" button;
4.0 Battery Level Warning
4.1 A battery charge level is displayed on the display panel;
4.2 If the battery is low on power, a text prompt "BATTERY LOW" is displayed on the display panel;
4.3 If the battery level is insufficient for 5 cycles the drain control device wont operate and a text prompt "CHANGE BATTERY" appears on the display panel.

Aspects of the present invention have been described by way of example only and it should be appreciated that modifications and additions may be made thereto without departing from the scope thereof as defined in the appended claims.

The claims defining the invention are:

1. A sterilisation apparatus for the sterilisation of medical equipment which includes:
    a sterilisation compartment formed from at least one wall and base;
    a spill compartment formed from at least one wall and base;
    a drain outlet and associated valve adapted so as to drain the sterilisation fluid from the sterilisation compartment and/or the spill compartment;
    a drain control device releasably engaged with the drain outlet and is configured to operate the opening and closing of the drain outlet to control exposure time of the equipment to the sterilisation fluid; and
    a display device;
    wherein the at least one wall of the sterilisation compartment is/are contained within the at least one wall of the spill compartment;
    wherein the drain control device includes a timer to time exposure of the medical equipment to the sterilisation fluid;
    wherein the drain control device includes a liquid level sensor so that the display device may indicate to a user when a preferred amount of sterilisation fluid has been added to the sterilisation apparatus.

2. A sterilisation apparatus as claimed in claim 1 wherein the spill compartment is separated from the sterilisation compartment by a wall lower in height than that of the at least one wall of the sterilisation compartment.

3. A sterilisation apparatus as claimed in claim 1 wherein the sterilisation apparatus has profiling on the inside surface of the sterilisation apparatus via a contact means to contact and retain the equipment to hold the equipment substantially above the sterilisation apparatus to maximise the exposure of the equipment with the sterilisation fluid.

4. A sterilisation apparatus as claimed in claim 3 wherein the contact means has a raised profile to provide a contact surface for the equipment in the sterilisation apparatus.

5. A sterilisation apparatus as claimed in claim 1 wherein the drain control device operates the opening and closing of the drain outlet via a clamp, clasp, catch, fastener or valve.

6. A sterilisation apparatus as claimed in claim 5 wherein the drain control device operates the opening and closing of the drain outlet via a valve.

7. A sterilisation apparatus as claimed in claim 1 wherein the drain control device includes a control device along with an optional display device.

8. A sterilisation apparatus as claimed in claim 1 wherein the drain control device follows an automatic override procedure wherein the sterilisation fluid is drained from the sterilisation compartment if the correct sequence of events of the sterilisation cycle is not followed.

9. A sterilisation apparatus as claimed in claim 1 wherein the drain control device logs the parameters of the previous sterilisation cycles.

10. A sterilisation apparatus as claimed in claim 1 wherein the sterilisation apparatus has a lid which engages with the sterilisation apparatus via a lid engagement means.

11. A sterilisation apparatus as claimed in claim 10 wherein the lower surface of the sterilisation apparatus is profiled so a portion of the lower surface may contact the sterilisation fluid when the sterilisation apparatus is filled and the lid engaged.

12. A method for timed sterilisation of medical equipment, using the sterilisation apparatus of claim 10,
    said sterilisation apparatus for the sterilisation of equipment including:
        a sterilisation compartment formed from at least one wall and base; and
        a spill compartment formed from at least one wall and base;
    said method for timed sterilisation of equipment including the steps:
        (a) removing the lid of the sterilisation apparatus;
        (b) placing the equipment in the sterilisation compartment;
        (c) adding sterilisation fluid to the equipment in the sterilisation compartment;
        (d) operating the control device to select the desired sterilisation time; and
        (e) removing the equipment from the sterilisation compartment following sterilisation for use.

13. A sterilisation apparatus as claimed in claim 1 wherein the outer wall of the sterilisation apparatus has an exit for a cable of medical equipment to be sterilised.

14. A sterilisation apparatus as claimed in claim 1 wherein the sterilisation apparatus has an associated container which releasably attaches to the sterilisation compartment so that its upper edges are lower than or flush with the upper edge of the sterilisation compartment.

15. A kit assembly of the sterilisation apparatus as claimed in claim 1 wherein the sterilisation apparatus is sold together with a jug for preparation of the chlorine dioxide solution before use.

* * * * *